United States Patent [19]

Lewis

[11] Patent Number: 5,955,643
[45] Date of Patent: Sep. 21, 1999

[54] COMPOSITION AND METHOD FOR INHIBITING POLYMERIZATION DURING THE ANAEROBIC OF STYRENE

[75] Inventor: Vincent E. Lewis, Missouri City, Tex.

[73] Assignee: Nalco/Exxon Energy Chemicals, L.P., Sugar Land, Tex.

[21] Appl. No.: 08/953,427

[22] Filed: Oct. 17, 1997

[51] Int. Cl.$^6$ ...................................................... C07C 7/20
[52] U.S. Cl. ............................................................ 585/899
[58] Field of Search ............................................ 585/899

[56] References Cited

U.S. PATENT DOCUMENTS

| | | | |
|---|---|---|---|
| 4,466,905 | 8/1984 | Butler et al. ............................ | 252/403 |
| 4,670,131 | 6/1987 | Ferrell ..................................... | 208/48 |
| 5,254,760 | 10/1993 | Winter et al. .............................. | 585/5 |
| 5,312,952 | 5/1994 | Grossi et al. ............................. | 558/46 |
| 5,396,004 | 3/1995 | Arhancet et al. .......................... | 585/5 |
| 5,648,574 | 7/1997 | Arhancet et al. .......................... | 585/5 |

*Primary Examiner*—Johann Richter
*Assistant Examiner*—Joseph Murray
*Attorney, Agent, or Firm*—Kelly L. Cummings; Thomas M. Breininger

[57] ABSTRACT

Polymerization is inhibited during the anaeroic production of styrene through the addition of a combination of a stable nitroxide free radical compound and a non-toxic phenylenediamine compound.

6 Claims, 3 Drawing Sheets

COMPOSITION AND METHOD FOR INHIBITING POLYMERIZATION DURING THE ANAEROBIC OF STYRENE

FIELD OF THE INVENTION

This invention relates generally to styrene antifoulants and, more particularly, to a composition and method for inhibiting polymerization during the anaerobic production of styrene.

BACKGROUND OF THE INVENTION

Vinyl aromatic monomers, such as styrene, are used extensively for the manufacture of plastics. These monomers undergo undesirable thermal and free radical polymerization during storage, shipping, and particularly during processing. Such polymerization can cause fouling of distillation towers and other equipment used for processing the monomers and can render the monomers unfit for use without further treatment. Accordingly, to minimize polymerization, compounds having polymerization inhibiting activity are commonly added to the monomer recovery stream.

A wide variety of compounds are known in the art and have been employed as polymerization inhibitors. However, while some of these compounds can actually inhibit polymerization (hereinafter referred to as "true inhibitors"), others can merely slow down the polymerization process (hereinafter referred to as "retarders").

True inhibitors completely inhibit polymerization for the period of time during which they are present in the styrene stream. The most frequently utilized true inhibitors are stable nitroxide free radical compounds. U.S. Pat. No. 4,670,131, which is representative of the prior art, discloses the use of stable free radicals, including nitroxides, to inhibit the polymerization of olefinic compounds, such as styrene. Nitroxides are generally recognized as the cornerstone of inhibitor programs because of their superior inhibiting capabilities. Other inhibitors, such as alkyl hydroxylamines, are not as effective in styrene systems at the desired levels.

Unfortunately, true inhibitors are consumed during the course of their activity. This means that following complete consumption, polymerization occurs as if the system was never treated. Therefore, in a plant emergency where the flow of styrene antifoulant is lost, a distillation tower treated with a true inhibitor will become an untreated tower in a very short period of time. This is particularly problematic as polymerization can continue and in effect turn the inside of the tower into solid polystyrene.

Retarders, unlike true inhibitors, do not stop polymerization. Rather, retarders slow down the rate of polymer growth. The compounds commercially employed as retarders are dinitrophenols, such as 2,4- and 2,6-dinitrophenol, as well as alkylated homologues such as 2,4-dinitro-o-cresol and 2,4-dinitro-sec-butylphenol.

The advantage of using a retarder like dinitrophenol in a treatment program is that it is not rapidly consumed. This means that unconsumed retarder can generally be recycled in a styrene recovery process. Moreover, the lack of consumption enables the retarder to maintain distillation tower integrity for an extended period of time in the event of a plant emergency.

Therefore, combining a true inhibitor like nitroxide with dinitrophenolic retarder could effectively control polymerization, even during a plant emergency. The true inhibitor would inhibit polymerization while, in an emergency situation, the retarder would slow polymerization until the emergency could be treated. This type of inhibitor program has been disclosed in the prior art. For example, U.S. Pat. No. 5,254,760 teaches the use of a nitroxide in combination with an aromatic nitro compound, such as dinitro-o-cresol (DNOC), to inhibit the polymerization of styrene.

Unfortunately, although dinitrophenols, such as DNOC, are effective retarders, they are extremely toxic. In addition, dinitrophenols have very low solubility, i.e., less than 5%, in both styrene and its precursor ethylbenzene. Companies that use either of these two products typically make up solutions in hot styrene or ethylbenzene to increase solubility. However, the companies are then dealing with a known toxin dissolved in a hot carcinogen. Although solubility problems can be overcome by using products such as dinitro-sec-butylphenol, the alkyl group does not add any activity to the product. Therefore, while solubility in the hydrocarbons is increased, product activity is decreased.

Furthermore, styrene manufacturers have gone to great lengths to remove air from the product recovery section of their plants. Thus, an inhibitor system must work under anaerobic conditions. The term "anaerobic" is used herein to mean substantially free of oxygen. In other words, although styrene manufacturers attempt to operate air-free processes, trace amounts of oxygen may nonetheless be present. Several known retarders, however, require the presence of oxygen to reduce the amount of polymerization which occurs. For example, U.S. Pat. No. 4,466,905 discloses that phenylenediamines and 2,6-dinitro-p-cresol will inhibit polymerization in the distillation column if oxygen is present.

Accordingly, it would be desirable to provide an improved composition and method for the inhibition of polymerization during the anaerobic production of styrene using a combination of a true inhibitor and a retarder. It would also be desirable to employ a stable nitroxide free radical compound as the true inhibitor and a non-toxic compound as the retarder.

SUMMARY OF THE INVENTION

The present invention calls for adding a combination of a stable nitroxide free radical compound and a non-toxic phenylenediamine compound to an anaerobic styrene process. This nitroxide/phenylenediamine combination effectively inhibits the polymerization of styrene.

DETAILED DESCRIPTION OF THE INVENTION

Figure 1:
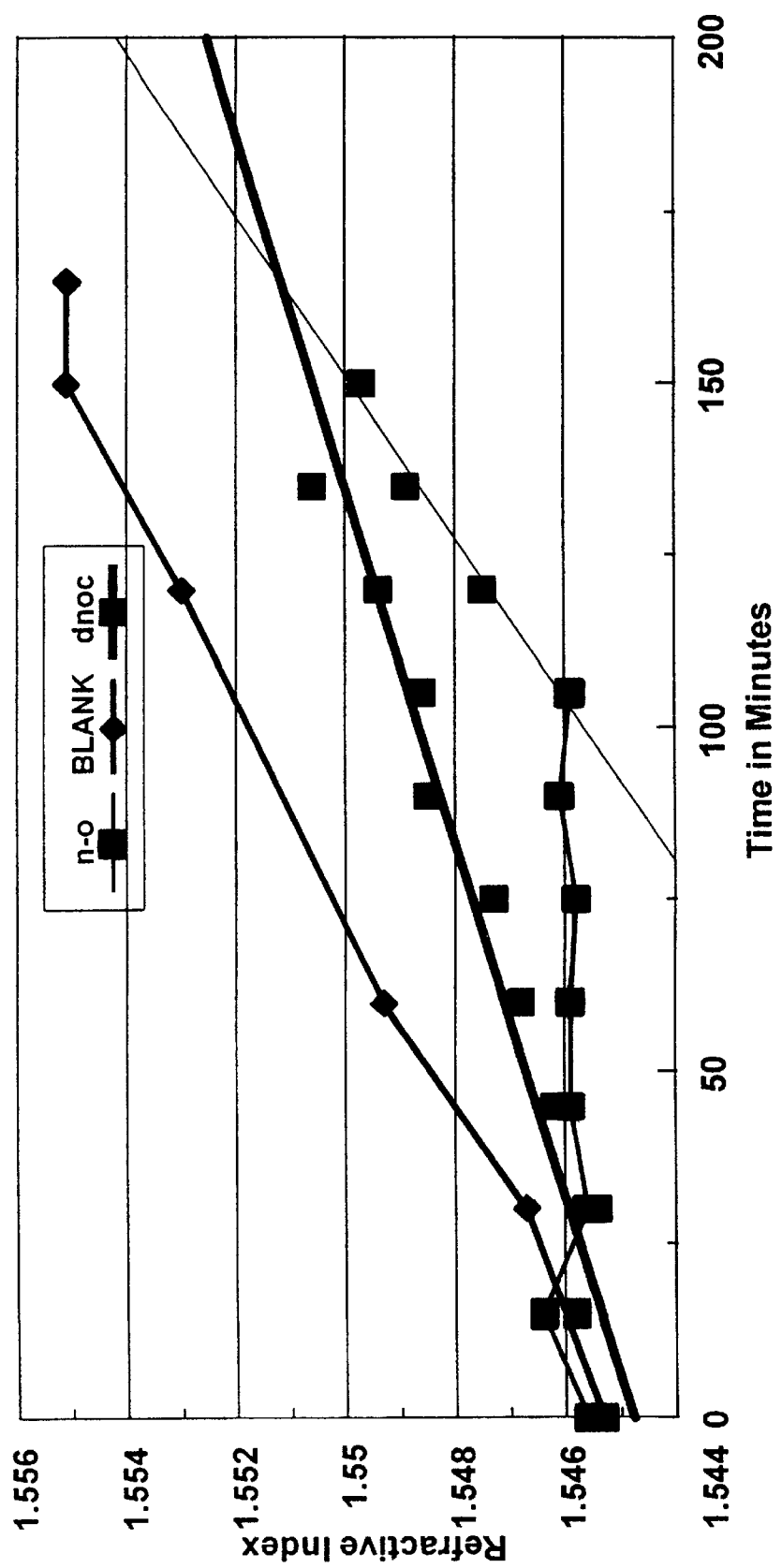
FIG. 1 shows a comparison between untreated styrene, a dinitrophenolic retarder and a nitroxide inhibitor.

The present invention is directed to a composition and method for inhibiting the polymerization of styrene. In accordance with this invention, a combination of a stable nitroxide free radical inhibitor and a non-toxic phenylenediamine retarder is added to an anaerobic styrene process.

The nitroxide free radical inhibitors which may be used in the practice of this invention are described in U.S. Pat. No.

5,254,760, the disclosure of which is incorporated herein by reference. It is believed that other nitroxide free radicals could also be used with suitable results. The preferred nitroxide free radical for use in inhibiting styrene polymerization under anaerobic conditions is 4-hydroxy-2,2,6,6-tetramethylpiperidin-1-oxyl (HTMPO).

The phenylenediamine retarders which may be employed in the practice of the present invention are described in U.S. Pat. No. 5,396,004, the disclosure of which is incorporated herein by reference. It is believed that other phenylenediamine retarders could also be used with suitable results. The preferred retarder is bis(1,4-dimethylpentyl)-p-phenylenediarnine (PDA).

The nitroxide/phenylenediamine inhibitor composition is used at a concentration which will effectively inhibit styrene polymerization under normal anaerobic operating conditions and slow polymerization in emergency situations. It is preferred that the total amount of the inhibitor composition be in the range of about 50 to about 1000 ppm based on the weight of styrene. More preferably, the total amount of the inhibitor composition is from about 100 ppm to about 500 ppm, with about 200 ppm to about 300 ppm being most preferred.

The nitroxide and phenylenediamine compounds can be introduced into the styrene process by any conventional method either separately or as a composition containing both components.

The present inventor has discovered that combining a stable nitroxide free radical such as HTMPO, which is a true inhibitor, and a retarder such as PDA provides the best of both types of styrene antifoulant. The true inhibitor completely inhibits styrene polymerization, while in an emergency situation, the retarder slows polymerization until the emergency can be treated. Moreover, when used in the appropriate combination, these two compounds have been shown to have superior retarder characteristics than dinitro-o-cresol (DNOC), which is an industry standard styrene antifoulant despite its undesirable toxicity.

EXAMPLES

The following examples are intended to be illustrative of the present invention and to teach one of ordinary skill how to make and use the invention. These examples are not intended to limit the invention or its protection in any way.

Example 1

Method for Evaluating a Styrene Polymerization Inhibitor

TBC Removal

T-butylcatechol (TBC) was removed from commercial styrene samples by passing the samples through an ion exchange column. Confirmation of TBC removal was obtained by shaking an aliquot of styrene with a 5% sodium hydroxide solution. The appearance of a yellow color indicated that TBC was still present, while a colorless solution indicated that all of the TBC had been removed.

Oxygen Removal

An evaluation of styrene antifoulants was conducted under inert atmosphere. To that end, the styrene samples were degassed using a freeze-thaw method. In accordance with this method, a 5 mL aliquot of TBC-free styrene was placed inside a polymerization tube and dosed with the appropriate amount of antifoulant. The tube was sealed using a screw cap with a gas-tight fitting. It was then placed in a dry ice/acetone bath ($-78°$ C.), and the styrene was allowed to freeze ($-31°$ C. melting point). Once the styrene froze, the polymerization tube was removed from the bath and attached to a vacuum pump via a Firestone valve (i.e., a 3-way valve designed for degassing liquids by this method). The tube was then opened to vacuum (0.5 mm Hg). When the atmosphere in the tube equilibrated, the tube was again sealed and the vacuum source was removed.

The polymerization tube containing solid styrene under vacuum was set aside and the styrene was allowed to melt (thaw). As the styrene melted, bubbles of dissolved gas moved from the liquid to the gas phase. When the styrene completely melted, the tube was placed back in the dry ice/acetone bath and the freezing process was repeated.

This freeze-thaw method was carried out a total of three times. After the styrene had completely melted for the third time, the tube was again attached to the Firestone valve. The 3-way stopcock was turned such that the contents of the tube were exposed to argon. Opening the tube under argon enabled the tube vapor space to be filled with this inert gas.

Thus, all of the original atmosphere in the polymerization tube, including dissolved gasses, was replaced by argon without exposing the contents of the tube to open atmosphere. This method is known to remove 99.9+% of any oxygen that is present in the styrene sample.

Polymer Formation and Antifoulant Evaluation

A series of 10 samples were prepared in polymerization tubes in an identical fashion using equal amounts of styrene and antifoulant. Each sample represented a single data point. After degassing the samples, 9 out of 10 tubes were placed in a circulating oil bath at a specified temperature (usually between $110°$ C. and $130°$ C.). The tenth sample was left unheated and represented the data point at time zero.

The tubes were removed from the oil bath at regular intervals, and polymer growth was measured by the change in refractive index. The refractive index versus time was plotted to illustrate whether a particular compound was a retarder or an inhibitor. If there was an induction period, the compound was shown to be an inhibitor. On the other hand, if polymerization was only slowed down and not stopped (i.e., there was no induction period), then the compound was shown to be a retarder. The plots also provide the length of the induction period for a specified set of conditions (i.e., the dosage and temperature of the oil bath).

Example 2

Three sets of 10 polymerization tubes were prepared as described above in Example 1. Each tube was charged with 5 mL of TBC-free styrene. One set was left untreated and represented the Blank. Another set was dosed with 25 ppm of DNOC as a 1% solution in toluene, and another set was dosed with 25 ppm of HTMPO, also as a 1% solution in toluene.

Each polymerization tube was degassed and then heated in a circulating oil bath at a constant temperature of $110°$ C. Samples were removed at 15 minute intervals starting at time zero and the refractive index was measured for each sample. As shown in FIG. 1, the untreated styrene (Blank) polymerized in a relatively linear fashion, the DNOC retarder slowed down the rate of polymer growth, but did not stop polymerization, and the HTMPO inhibitor (i.e., nitroxide "n-o") had an induction period of approximately 50 minutes under these conditions, after which time it was consumed and polymerization creased as if the samples were never treated. Extrapolation of the graphs in FIG. 1 also shows that after about 170 minutes, the samples containing inhibitor contained more polymer than those containing retarder.

Example 3

Two sets of 10 polymerization tubes were prepared as described above in Example 1. Each tube was charged with 5 mL of TBC-free styrene. One set was dosed with 25 ppm of DNOC using a 1% solution in toluene. The other set was dosed with 25 ppm of PDA as a 1% solution in toluene.

Figure 2:
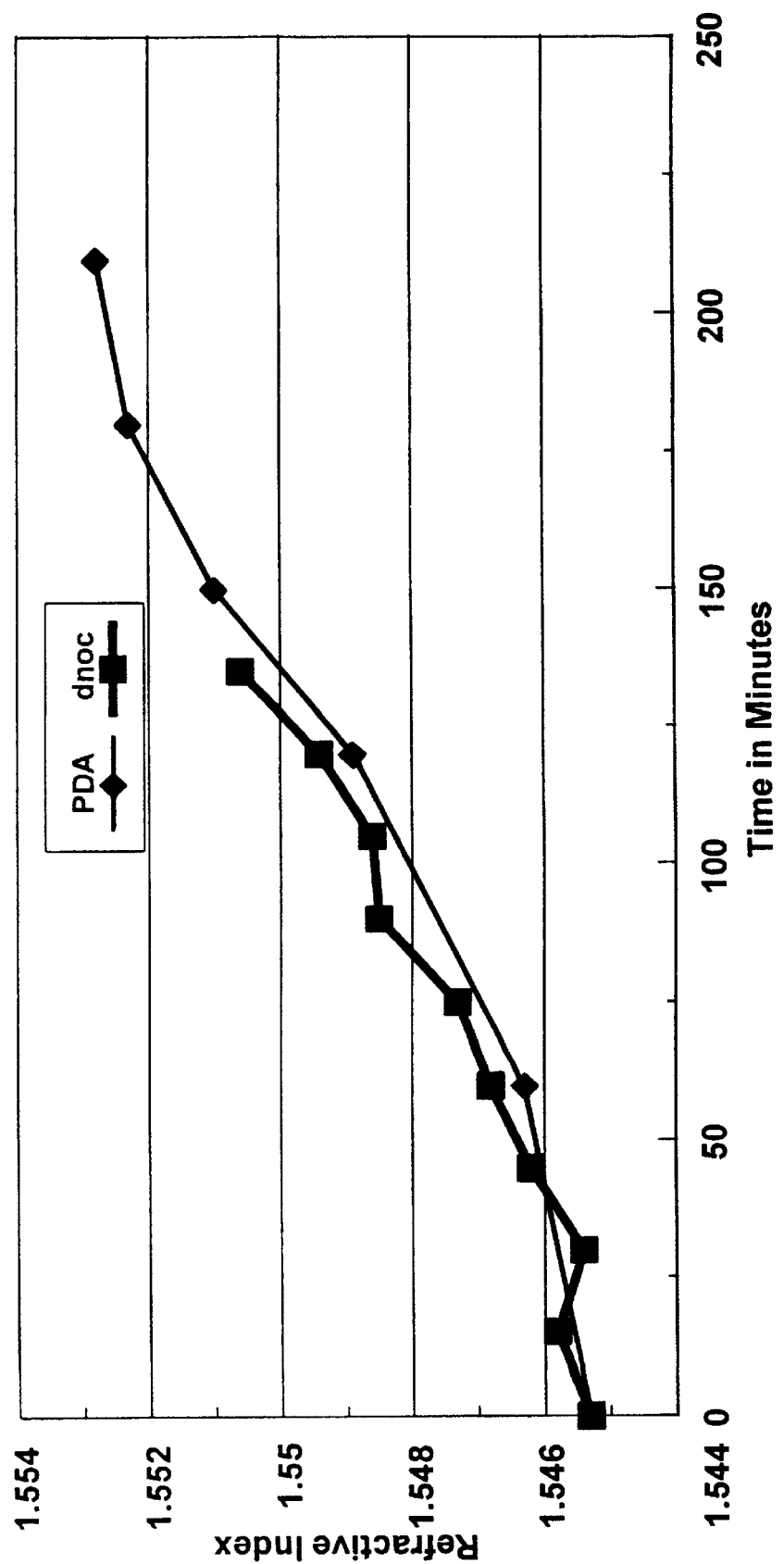
FIG. 2 shows a comparison between a phenylenediamine retarder and a dinitrophenolic retarder.

Each polymerization tube was degassed and then heated in a circulating oil bath at a constant temperature of 110° C. Samples were removed at 15 minute intervals starting at time zero and the refractive index was measured for each sample. FIG. 2 shows that because polymerization was only slowed down and not stopped (i.e., there was no induction period), both DNOC and PDA are retarders. FIG. 2 also shows that under these test conditions, PDA is not quite as good a retarder as DNOC.

Example 4

Two sets of 10 polymerization tubes were prepared as described above in Example 1. Each tube was charged with 5 mL of TBC-free styrene. One set was dosed with 25 ppm of DNOC using a 1% solution in toluene. The other set was dosed with 25 ppm of HTMPO as a 1% solution in toluene and with 50 ppm of PDA, also as a 1% solution in toluene.

Figure 3:
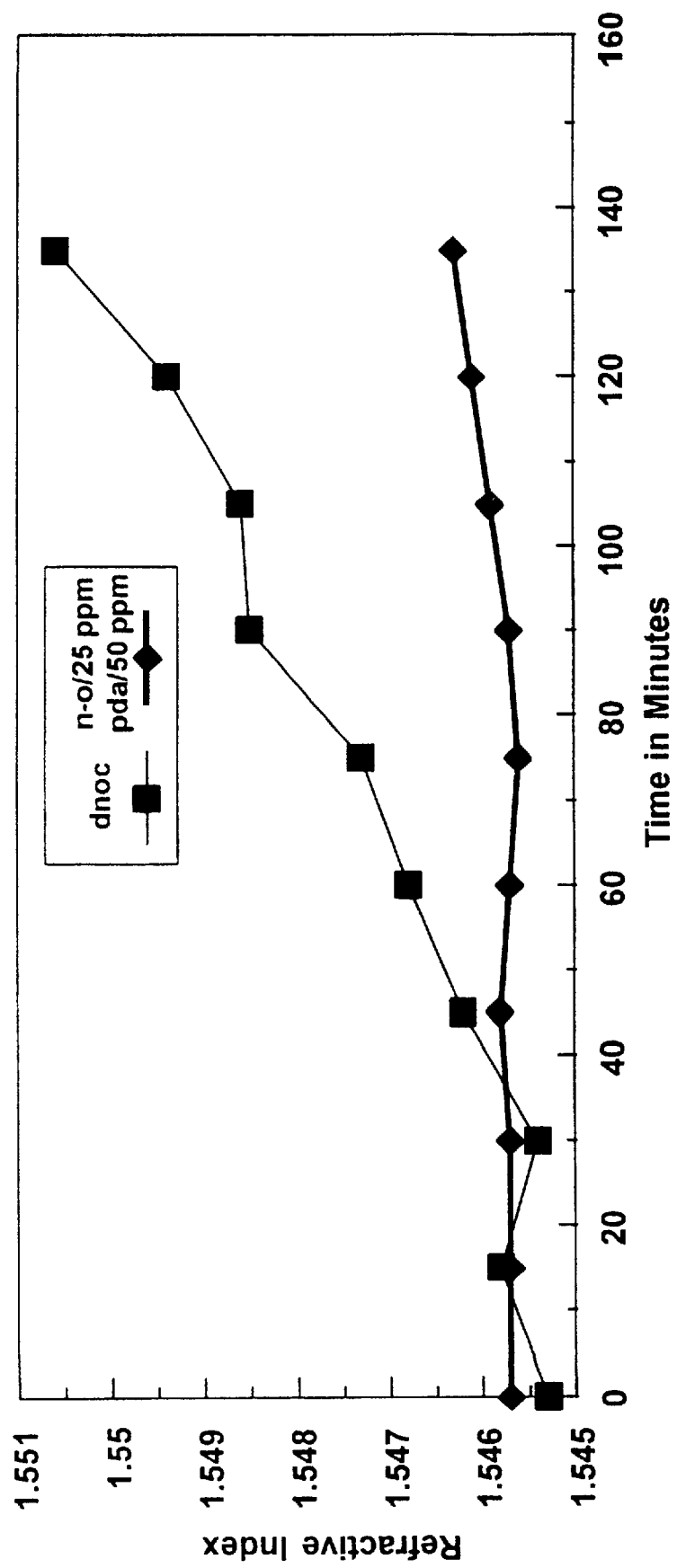
FIG. 3 shows a comparison between a dinitrophenolic retarder and a combination of a nitroxide inhibitor and a phenylenediamine retarder.

Each polymerization tube was degassed and then heated in a circulating oil bath at constant temperature of 110° C. Samples were removed at 15 minute intervals starting at time zero and the refractive index was measured for each sample. As shown in FIG. 3, the inventive combination of a stable nitroxide inhibitor (HTMPO) and a phenytenediamine retarder (PDA) is a much more effective styrene antifoulant under anaerobic conditions than DNOC alone. The inhibitor was active for about 75 minutes and there was no polymer present in the samples treated with the combined product. Unlike the inhibitor depicted in FIG. 1, which exhibited rapid polymer build-up after it was consumed at about 50 minutes, the HTMPO/PDA product still contained the retarder even after the inhibitor was consumed, thus greatly reducing the rate of polymer growth.

While the present invention is described above in connection with preferred or illustrative embodiments, these embodiments are not intended to be exhaustive or limiting of the invention. Rather, the invention is intended to cover all alternatives, modifications and equivalents included within its spirit and scope, as defined by the appended claims.

What is claimed is:

1. A method of inhibiting polymerization during the anaerobic production of styrene which comprises the step of incorporating therein an effective inhibiting amount of a combination of a stable nitroxide free radical compound and a phenylenediamine compound.

2. The method of claim 1 wherein the stable nitroxide free radical compound is 4-hydroxy-2,2,6,6-tetramethylpiperidin-1-oxyl.

3. The method of claim 1 wherein the phenylenediamine compound is bis (1,4-dimethylpentyl)-p-phenylenediamine.

4. The method of claim 1 wherein the combination of the nitroxide and phenylediamine compounds is added to the styrene in an amount from about 50 ppm to about 1000 ppm based on the weight of the styrene.

5. The method of claim 1 wherein the combination of the nitroxide and phenylediamine compounds is added to the styrene in an amount from about 100 ppm to about 500 ppm based on the weight of the styrene.

6. The method of claim 1 wherein the combination of the nitroxide and phenylediamine compounds is added to the styrene in an amount from about 200 ppm to about 300 ppm based on the weight of the styrene.

* * * * *